United States Patent [19]
Grunenberg et al.

[11] Patent Number: 5,849,752
[45] Date of Patent: *Dec. 15, 1998

[54] CRYSTAL MODIFICATION OF CDCH A PROCESS FOR ITS PREPARATION AND PHARMACEUTICAL FORMULATIONS COMPRISING THIS MODIFICATION

[75] Inventors: Alfons Grunenberg, Dormagen; Patrick Bosché, Odenthal, both of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 760,543

[22] Filed: Dec. 5, 1996

[30] Foreign Application Priority Data

Dec. 12, 1995 [DE] Germany .................. 195 46 249.1

[51] Int. Cl.⁶ ................... A61K 31/47; C07D 47/04
[52] U.S. Cl. ........................... 514/300; 546/113
[58] Field of Search .............. 514/300; 546/113

[56] References Cited

U.S. PATENT DOCUMENTS 5,480,879   1/1996   Petersen et al. .

FOREIGN PATENT DOCUMENTS

| 67463/87 | 7/1987 | Australia . |
| 0 241 206 A2 | 10/1987 | European Pat. Off. . |
| 0 342 649 A2 | 11/1989 | European Pat. Off. . |
| 0 550 903 A1 | 7/1993 | European Pat. Off. . |
| 0 603 887 A2 | 6/1994 | European Pat. Off. . |
| 0 629 621 A1 | 12/1994 | European Pat. Off. . |
| 0 643 058 A1 | 3/1995 | European Pat. Off. . |

*Primary Examiner*—Patricia L. Morris
*Attorney, Agent, or Firm*—Sprung Kramer Schaefer & Briscoe

[57] ABSTRACT

The invention relates to the new monohydrate of 1-cyclopropyl-7-([S,S]-2,8-diazabicyclo-[4.3.0]non-8-yl)6-fluoro-1,4-dihydro-8-methoxy-4-oxo-3-quinolinecarboxylic acid hydrochloride (CDCH), a process for its preparation and pharmaceutical formulations which comprise this monohydrate as the active compound.

10 Claims, 8 Drawing Sheets

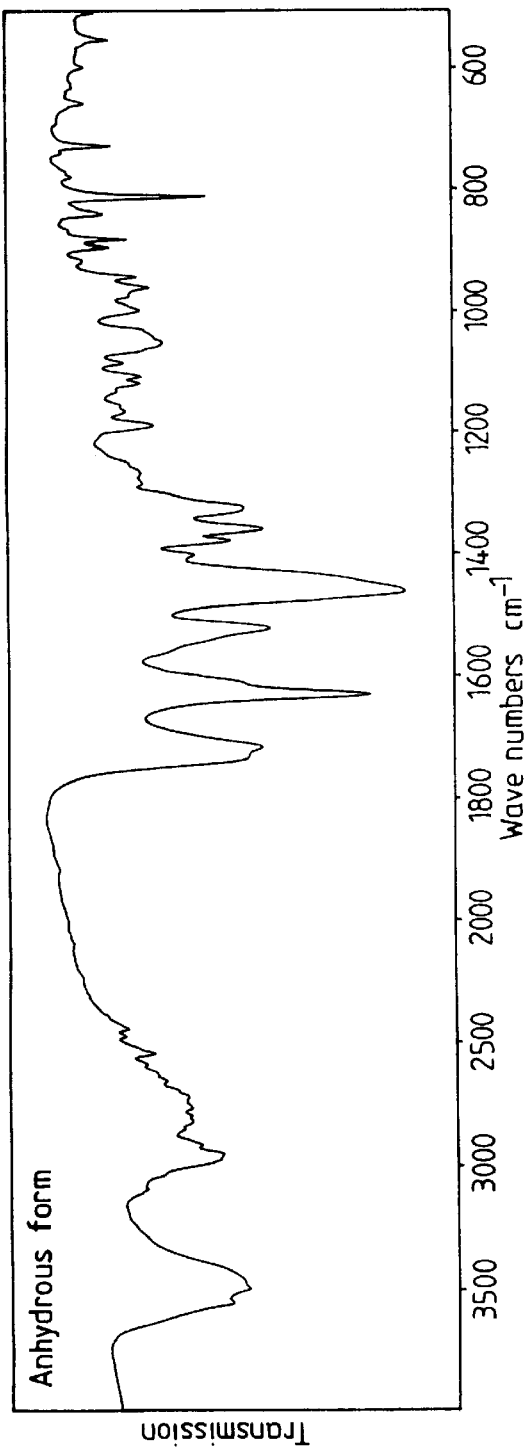
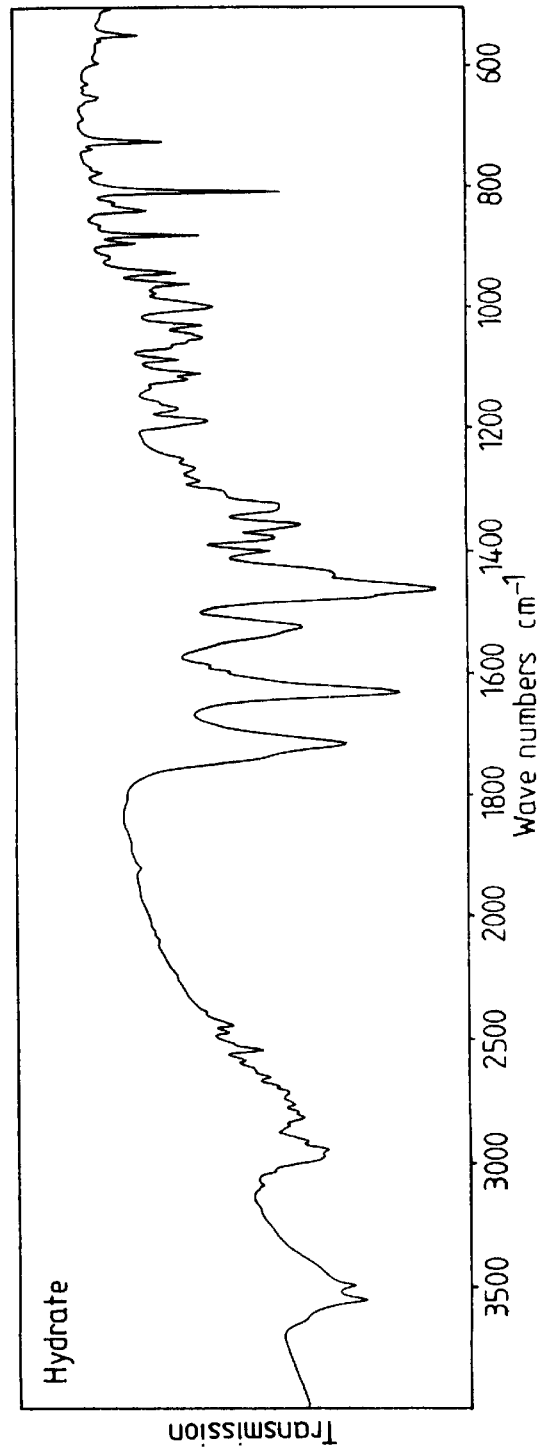

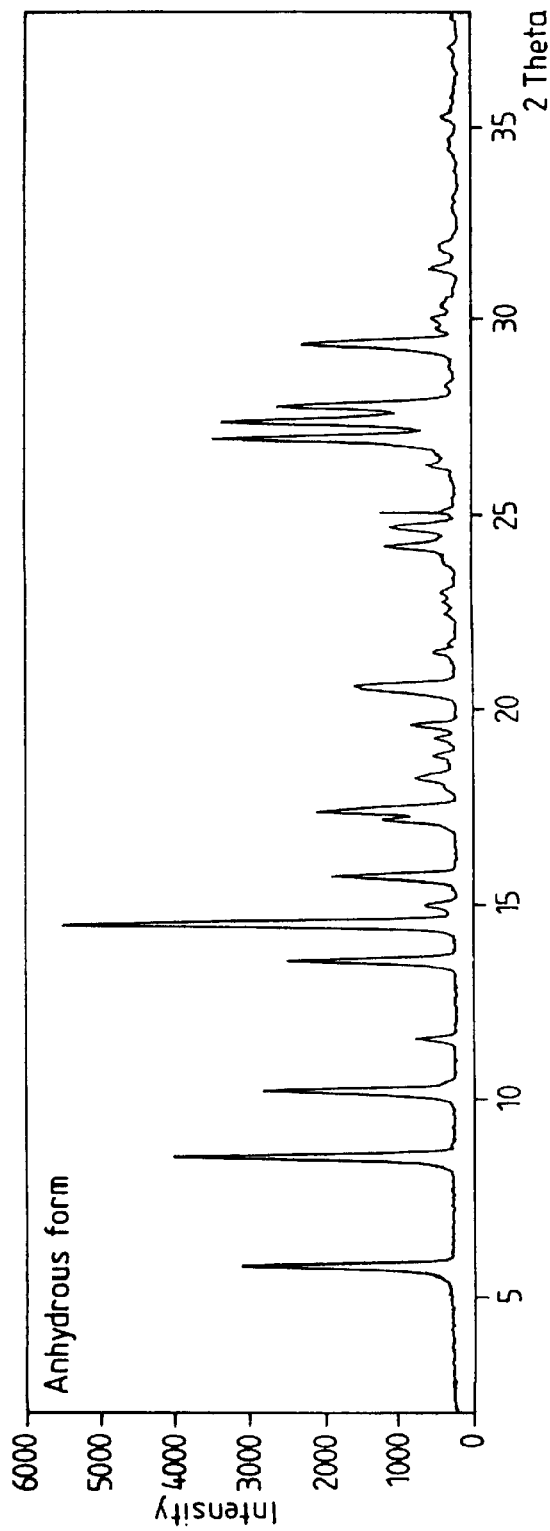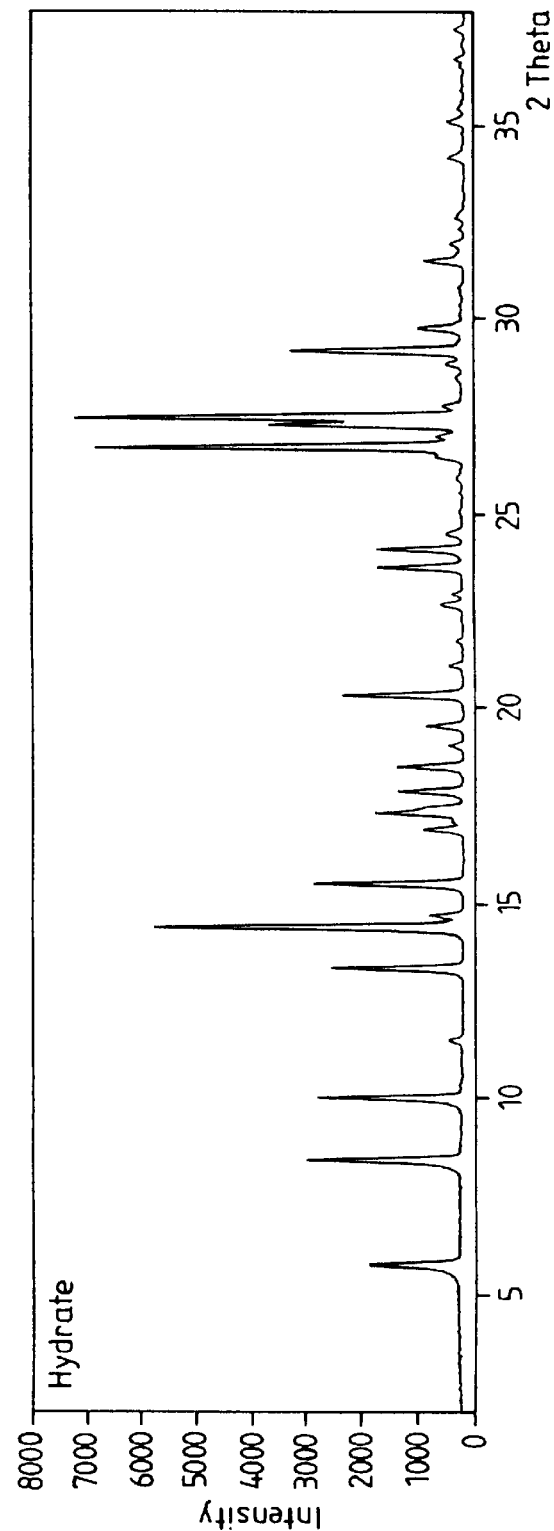

Anhydrous form

Hydrate

CRYSTAL MODIFICATION OF CDCH A PROCESS FOR ITS PREPARATION AND PHARMACEUTICAL FORMULATIONS COMPRISING THIS MODIFICATION

BACKGROUND OF THE INVENTION

1. Field of the Invention

The invention relates to the new monohydrate of 1-cyclopropyl-7-([S,S]-2,8-diazabicyclo-[4.3.0]non-8-yl)6-fluoro-1,4-dihydro-8-methoxy-4-oxo-3-quinolinecarboxylic acid hydrochloride (CDCH), a process for its preparation and pharmaceutical formulations which comprise this monohydrate as the active compound.

2. Description of Related Art

CDCH is a chemotherapeutic for humans and animals which has a broad spectrum of antibacterial action. The active compound can also be employed in the preservation of materials. CDCH shows a low toxicity and is particularly effective against Enterobacteriacea, and especially against antibiotic resistant strains: S. aureus, Ps. aeruginosa, Enterococcus faecalis and E. coli. CDCH and its preparation as a betaine is described in EP-A-550 903 and EP-A-591 808.

An anhydrous form of CDCH is the only crystal modification known to date. However, this crystal modification is not entirely satisfactory in the preparation of various medicament forms. CDCH is hygroscopic and absorbs water under adverse storage conditions and during pharmaceutical processing of the active compound to medicament forms. This impairs the dosing accuracy and quality of the preparations. Subsequent changes in the crystal structure of the anhydrous form when CDCH is stored in aqueous suspensions or at ambient humidity are the reason for the physical instability of CDCH. It is therefore of great importance to use a crystal form which is as stable as possible for the preparation of medicament forms comprising CDCH.

SUMMARY OF THE INVENTION

It has now been found that CDCH can be converted into a new water-containing crystalline modification which is distinguished by an increased stability, in particular during storage at high humidities, compared with the known anhydrous form and is particularly suitable for the preparation of stable pharmaceutical preparations.

During preparation of the monohydrate from aqueous media, the active compound crystallizes in the form of needles which become severely matted. Surprisingly, the crystal habit can be modified in a controlled manner under certain crystallization conditions. The prisms thus formed represent a preferred embodiment of the present invention, since they do not mat and are significantly more free-flowing than the monohydrate in the form of needles. This has considerable advantages in the preparation of medicament forms. By using a non-hygroscopic, free-flowing active compound, a satisfactory dosing accuracy is achieved during the preparation of medicaments, which increases safety and therefore minimizes the risk to the patient.

The invention accordingly relates to the new monohydrate of CDCH of the formula I

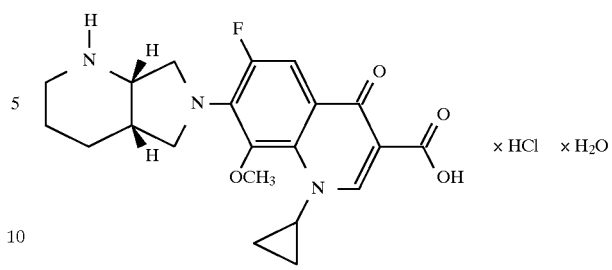

and to a process for its preparation, which is characterized in that anhydrous, crystalline CDCH is treated with an amount of water sufficient for thorough mixing and for formation of the monohydrate at temperatures below 80° C. until the stoichiometric content of water of crystallization has been absorbed and conversion of the crystals is complete, and the crystals thus obtained are separated off and dried to the constant weight of the monohydrate in order to remove the adsorbed water present. To avoid the formation of the anhydrous form, the humidity during drying should be not less than 30% relative humidity. The monohydrate crystallizes in the form of needles from water-containing media with a water content of more than 10%.

BRIEF DESCRIPTION OF THE DRAWINGS

The invention will now be described in further detail with reference to the drawings, wherein:

FIG. 1 consists of two IR spectra, wherein FIG. 1A is the IR spectrum of CDCH anhydrous form, and FIG. 1B is the IR spectrum of CDCH monohydrate;

FIG. 2 consists of two graphs depicting thermogravimetric weight loss, wherein

FIG. 3 consists of two thermograms, wherein

FIG. 4 consists of two X-ray diffractograms, wherein FIG. 4A is the X-ray diffractogram for CDCH anhydrous form, and FIG. 4B is the X-ray diffractogram for CDCH monohydrate;

FIG. 5 consists of two $^{13}$C-NMR spectra, wherein

FIG. 6 consists of two Raman spectra, wherein

FIG. 7 consists of two FIR spectra, wherein FIG. 8 consists of four photographs of microscopic CDCH, wherein

DESCRIPTION OF PREFERRED EMBODIMENTS

The preferred monohydrate form which crystallizes as prisms can be obtained by suspending anhydrous crystalline CDCH in ethanol/water mixtures, especially preferably in ethanol/water with a maximum of 10% of water, thorough mixing of the solid contents with the amount of water added being ensured until the required content of water of crystallization has been absorbed and conversion of the crystals is complete, for example by stirring the suspension or shaking, swirling, rotating the reaction vessel and the like. If the water content in the ethanol/water mixture is a maximum of 10%, the monohydrate crystallizes in the form of prisms.

Provided that the amount of water is sufficient for formation of a stoichiometric monohydrate and for thorough mixing of the amount of CDCH employed with the water, any desired amount of water can be used for formation of the monohydrate in the form of needles, since the absorption of water of crystallization, which proceeds with conversion of the crystals, ends with the formation of the monohydrate, and furthermore no further hydrates are obtained. The amount of water is expediently limited such that although thorough mixing can take place, no or low solubility losses occur. The preparation of the monohydrate is preferably carried out at room temperature, but can also be carried out at elevated temperature, for example 30° C. to 60° C., or a low temperature, for example 5° C. to 20° C. The preparation of the monohydrate from the anhydrous form also takes place successfully at humidities greater than 30% relative humidity. However, this process is not suitable for the preparation of the preferred monbhydrate which crystallizes as prisms.

The crystals of the monohydrate are separated off from the excess solvent by customary methods, for example by filtering, decanting, centrifuging and the like. The crystals of the monohydrate which have been separated off are advantageously dried at room temperature or at elevated temperature up to 50° C. at humidities of at least 30% relative humidity.

The CDCH monohydrate according to the invention has a characteristic IR spectrum (FIG. 1), which shows characteristic absorption bands of the water of crystallization in the region of the OH valency vibrations (3600–3100 $cm^{-1}$), which are absent in the anhydrous crystal modification. It also differs from the anhydrous CDCH in other frequency ranges, so that a completely different arrangement of the molecules in the crystal lattices of the two modifications can be concluded.

Figure 2A:
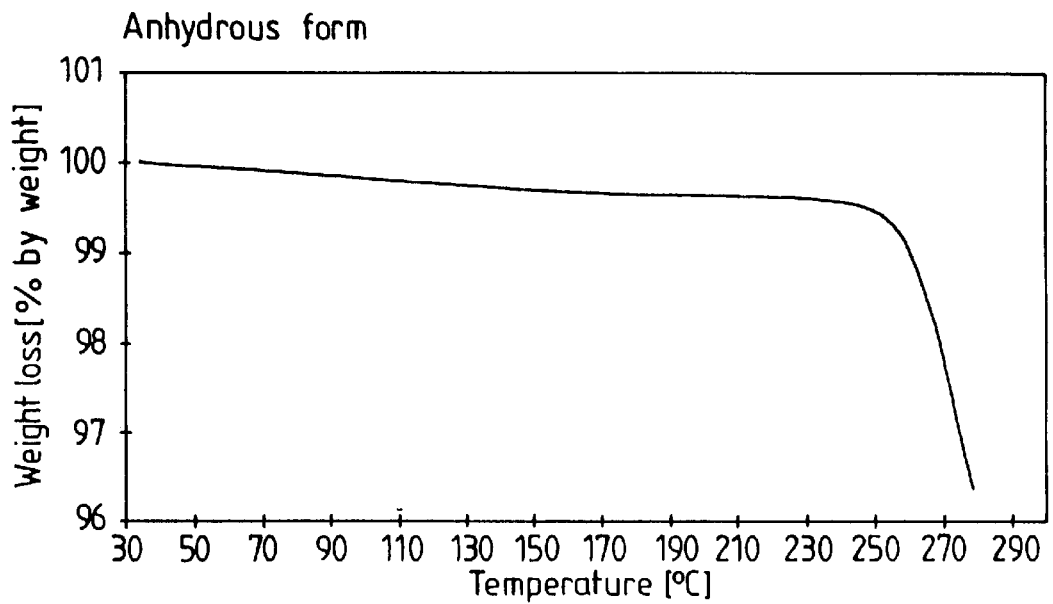
FIG. 2A shows the weight loss for CDCH anhydrous form.
Figure 2B:
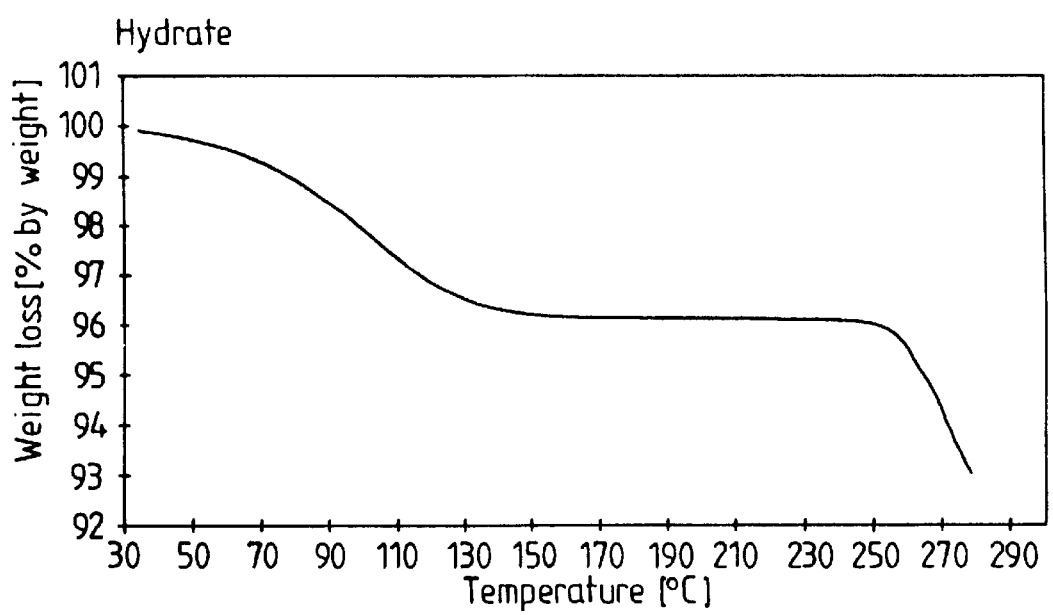
FIG. 2B shows the weight loss for CDCH monohydrate.
Figure 3A:
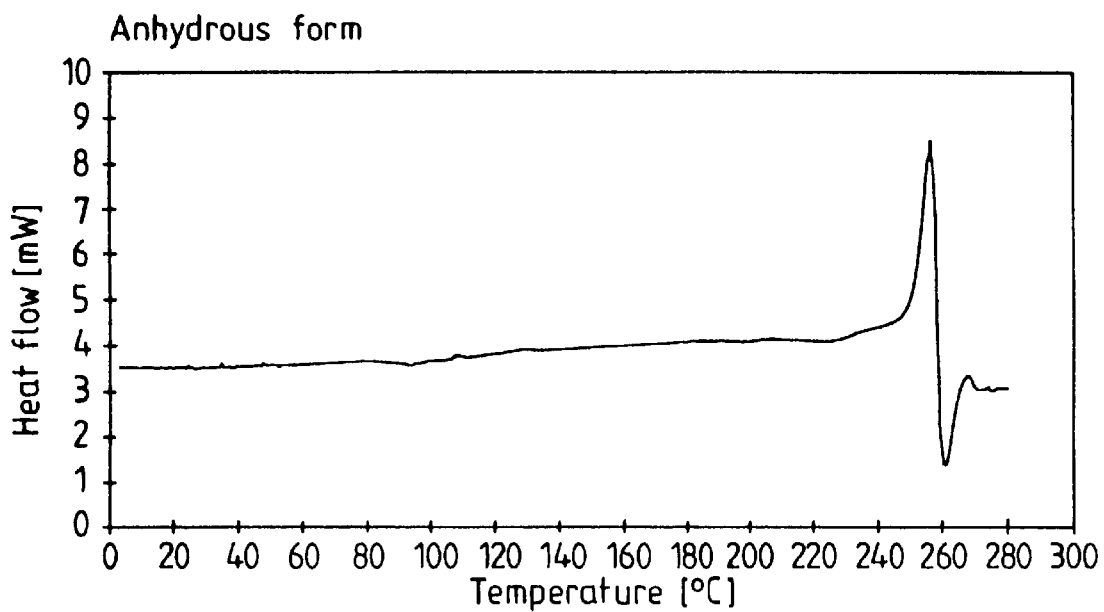
FIG. 3A is the thermogram for CDCH anhydrous form.
Figure 3B:
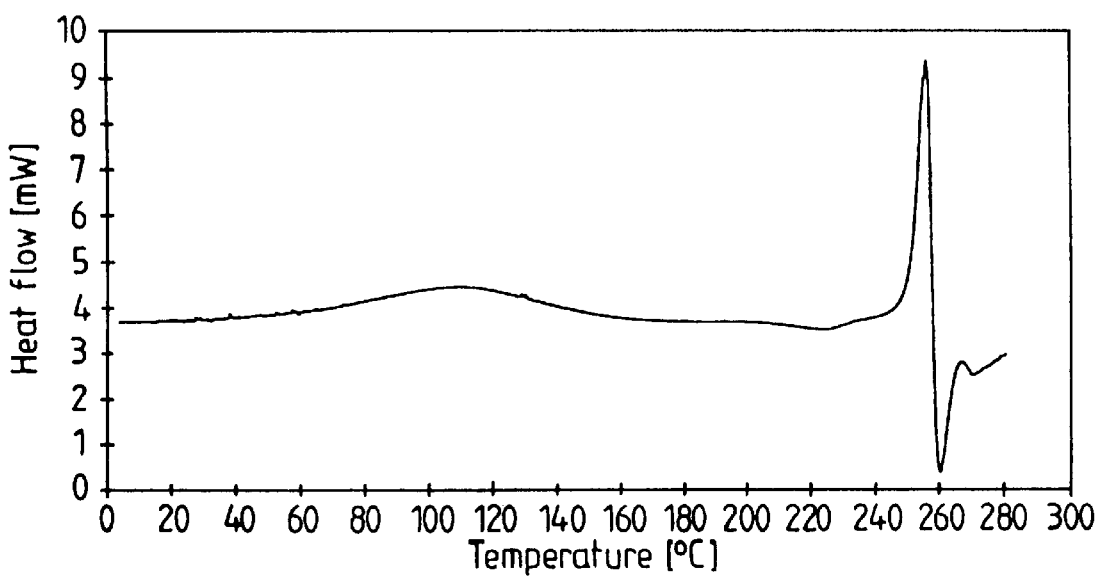
FIG. 3B is the thermogram for CDCH monohydrate.
Figure 5A:
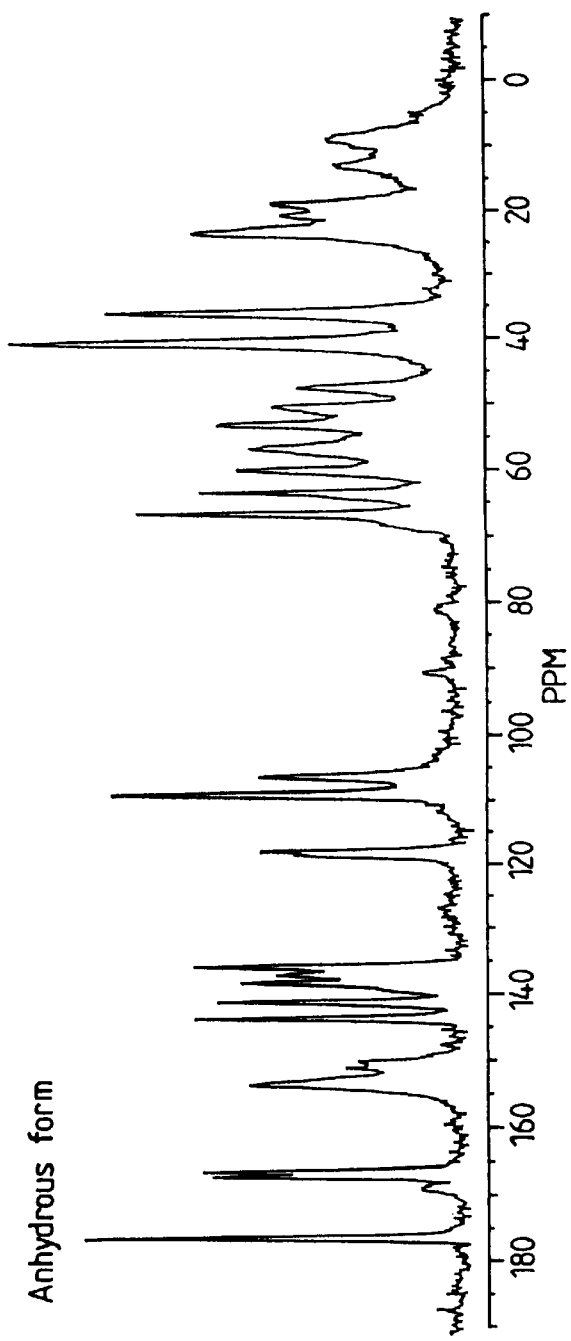
FIG. 5A is the $^{13}$C-NMR spectra for CDCH anhydrous form.
Figure 5B:
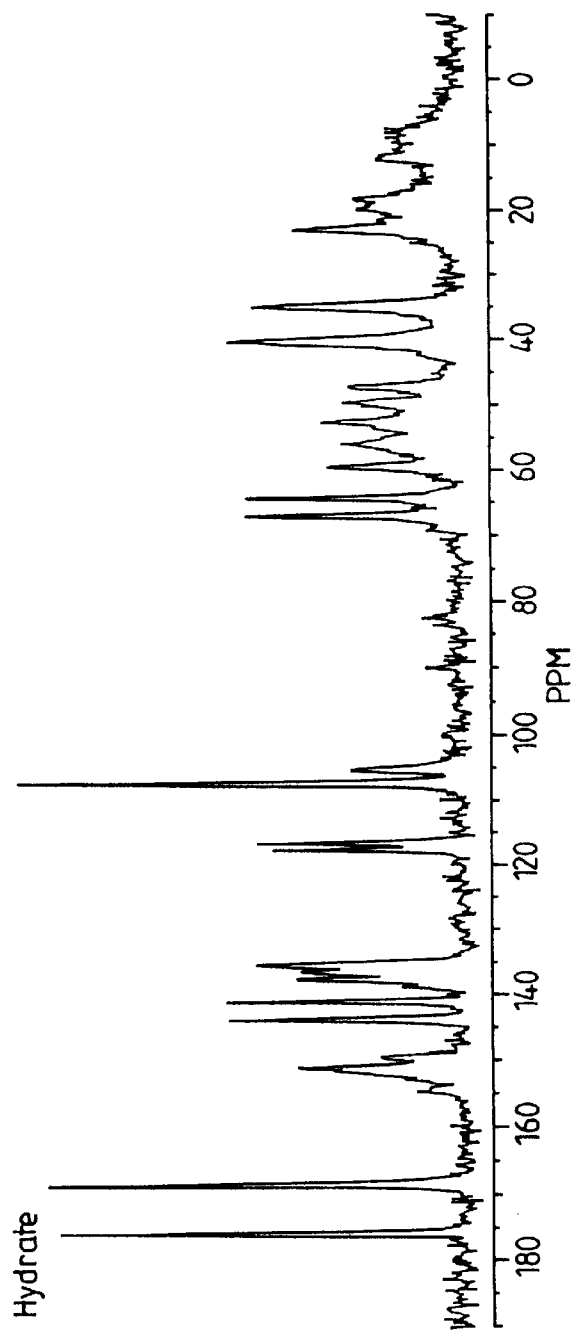
FIG. 5B is the $^{13}$C-NMR spectra for CDCH monohydrate.
Figure 6A:
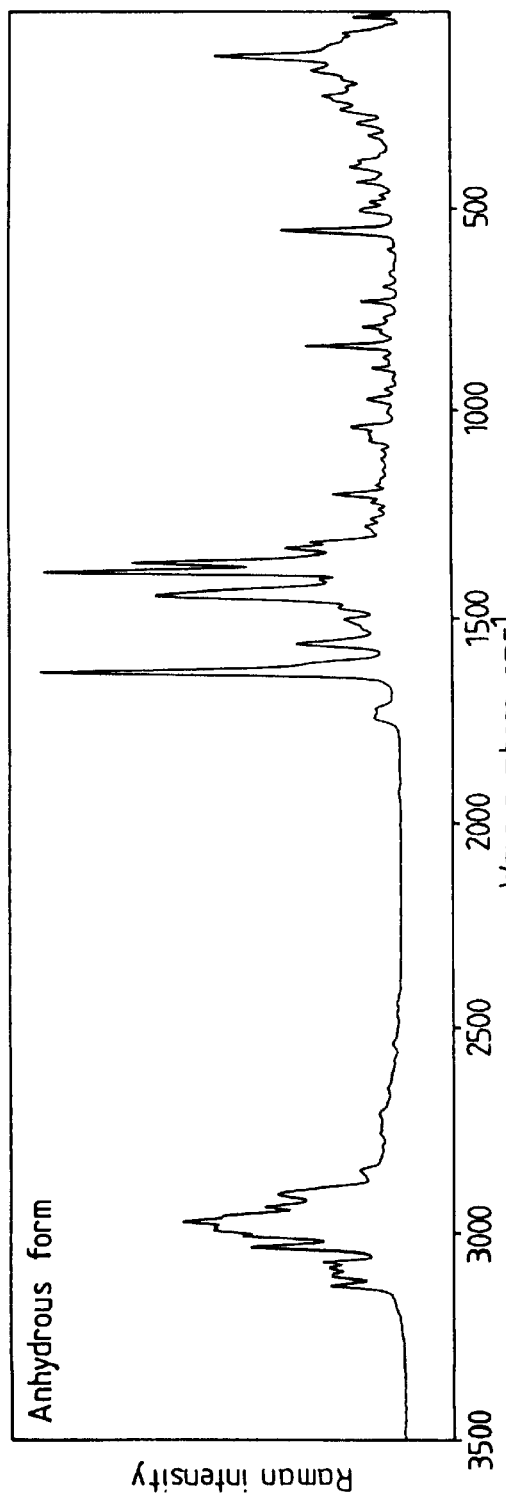
FIG. 6A is the Raman spectra for CDCH anhydrous form.
Figure 6B:
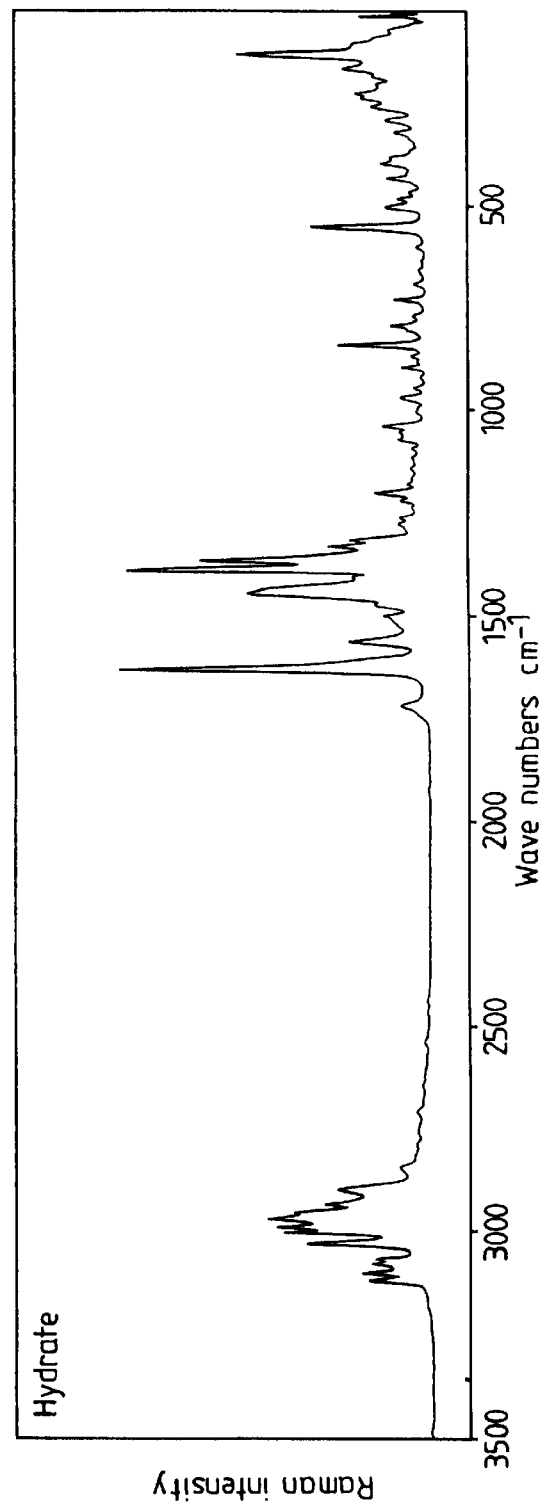
FIG. 6B is the Raman spectra for CDCH monohydrate.
Figure 7A:
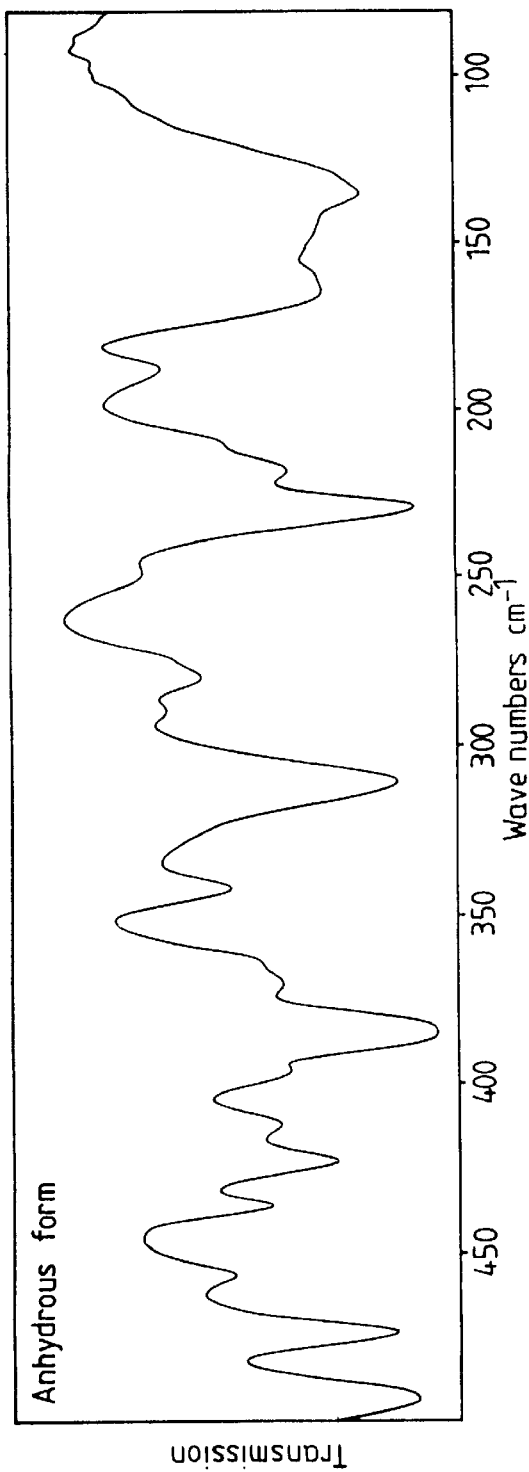
FIG. 7A is the FIR spectra for CDCH anhydrous form.
Figure 7B:
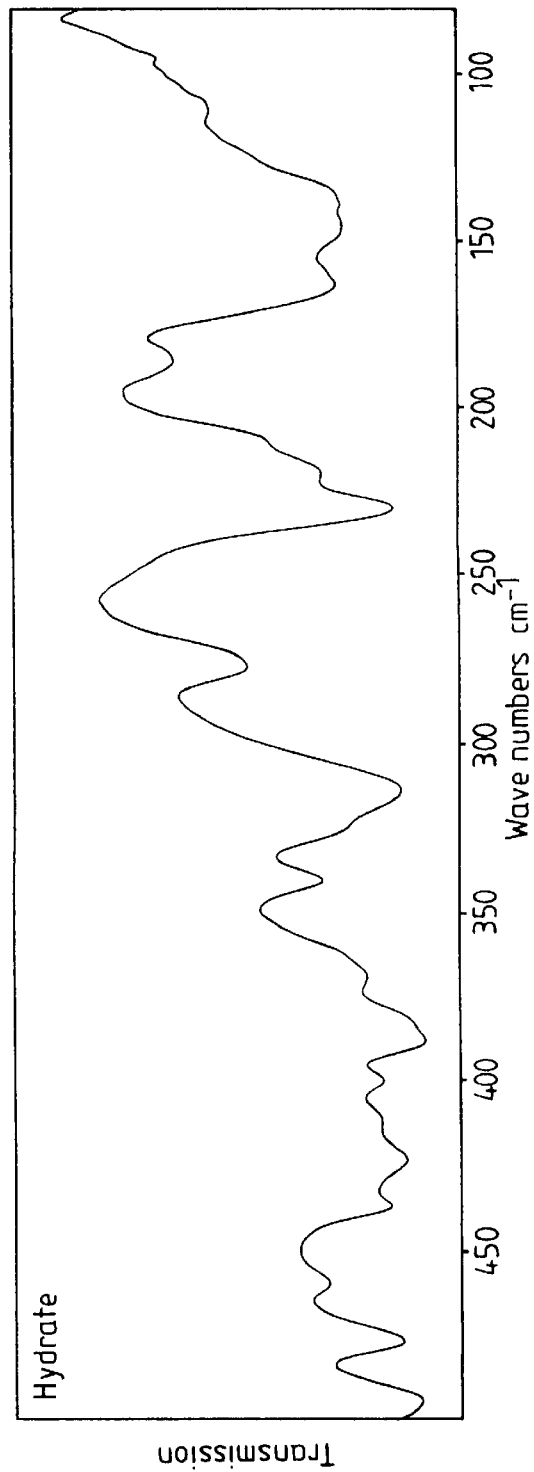
FIG. 7B is the FIR spectra for CDCH monohydrate.
Figure 8A:
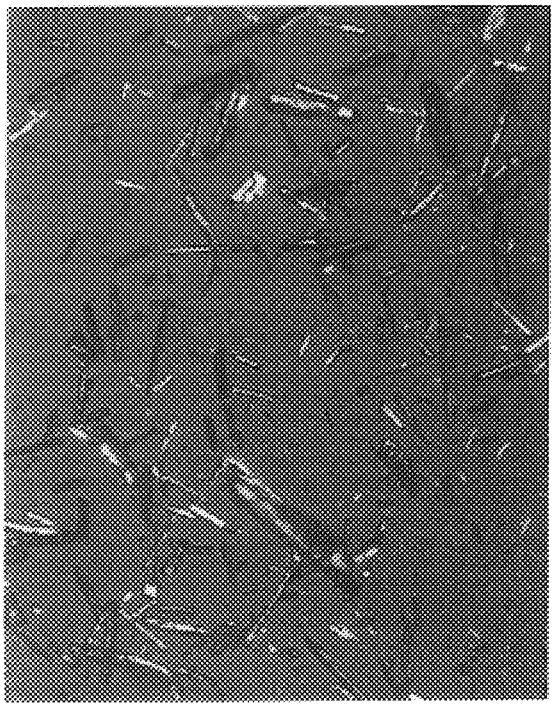
FIGS. 8A and 8B are photographs of CDCH needles.
Figure 8B:
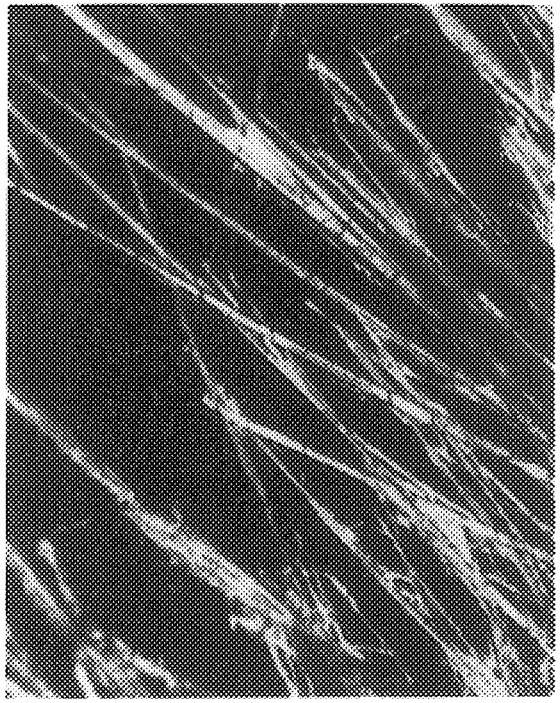
Figure 8C:
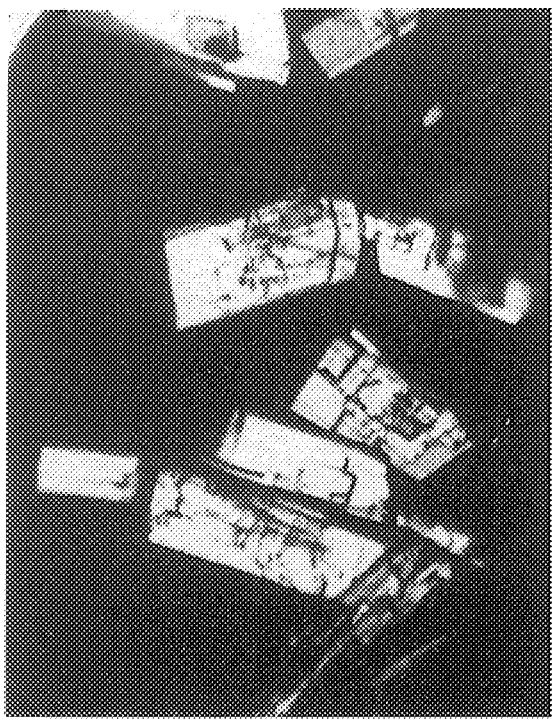
FIGS. 8C and 8D are photographs of CDCH prisms.
Figure 8D:
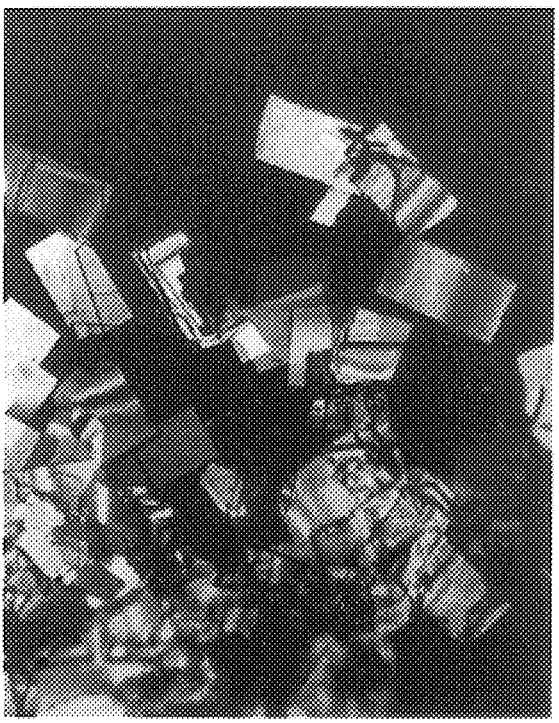

The determination of the water content confirms the presence of a stoichiometric monohydrate of CDCH. The thermogravimetric weight loss determined in several samples of the monohydrate is 1 mol of water (3.9%, FIG. 2). The thermogram of the monohydrate (FIG. 3) recorded by means of DSC (Differential Scanning Calorimetry) under atmospheric pressure shows, in agreement with the thermogravimetric measurements, the release of water by a broad endothermal peak which indicates the rearrangement of the crystal lattice of the monohydrate analysed, the dissociation of CDCH and water and the enthalpy of vaporization of the liberated water of crystallization. The X-ray diffractograms and $^{13}$C-NMR, Raman and FIR spectra of the anhydrous form and of the monohydrate show characteristic differences (FIGS. 4–7, Tables 2–5): thus, for example, the $^{13}$C-NMR spectrum has a characteristic peak at 168.1 ppm and the X-ray diffractogram a line at 2Θ=26.7.

The DSC and TGA thermograms were obtained using thermoanalysers (DSC 7 and TGA 7) from Perkin-Elmer. The X-ray diffractograms were recorded with a Stoe transmission diffractometer. The IR, FIR and Raman spectra were recorded with Fourier-IR spectrometers IFS 66 (IR), IFS 66v (FIR) and IFS 88 (Raman) from Bruker. The $^{13}$C-solid-NMR spectra were recorded with a Bruker MSL 300. The microscopic photographs were taken with a Laborlux S microscope from Leitz.

During storage, the CDCH monohydrate according to the invention shows a higher physical stability compared with the anhydrous crystal modification, and is therefore more suitable for the preparation of various medicament forms. The preferred monohydrate, which crystallizes in the form of prisms, furthermore imparts to CDCH excellent trickling and flow properties, which is of great advantage in the preparation of pharmaceutical formulations (FIG. 8). The invention therefore also relates to liquid and solid pharmaceutical formulations which comprise the CDCH monohydrate according to the invention, such as, for example, suspensions, emulsions, tablets, coated tablets, coated tablet cores, suppositories, hard or soft gelatin capsules and the like. Aqueous suspensions and tablets for oral administration preferably comprise the monohydrate according to the invention, particularly preferably in the prismatic crystal form.

CDCH can be present in these pharmaceutical formulations as the only active compound or can be combined with other antibacterially active substances.

Pharmaceutical formulations can comprise the CDCH monohydrate according to the invention by itself or in combination with several other active compounds, or be formulated together with auxiliaries and additives usually employed in pharmacy, such as tablet binders, fillers, preservatives, tablet disintegrating agents, flow regulating agents, plasticizers, wetting agents, dispersing agents, emulsifiers, solvents, flavourings and the like, to give presentation forms for oral, parenteral or rectal administration.

The pharmaceutical formulations are prepared in a manner known per se, for example by mixing, stirring, suspending, dispersing, emulsifying, and the like, the active compounds with or in the pharmaceutical auxiliaries and processing the components to pharmaceutically suitable presentation forms for oral, parenteral or rectal administration.

PREPARATION OF CYRSTALLINE CDCH (NEEDLES, PRISMS)

Example 1 (Prisms)

1 g of anhydrous CDCH is dissolved in 150 ml of absolute ethanol and the solution is filtered. The solution is heat treated at 60° C. until the solvent has evaporated completely. The crystals which have precipitated out are dried at room temperature/ambient humidity.

Example 2 (Prisms)

0.1 g of anhydrous CDCH is dissolved in 10 ml of ethanol (10% water content). The solution is heat treated at 60° C. until the solvent has evaporated completely. The crystals which have precipitated out are dried at room temperature/ambient humidity.

Example 3 (Prisms)

4 g of anhydrous CDCH are dissolved in 300 ml of ethanol (96%). The solvent is distilled off in a rotary evaporator at 60° C. under 120 mbar. The crystals are dried in a vacuum drying cabinet under 80 mbar at 105° C. for 2 hours and then exposed to ambient humidity.

Example 4 (Needles)

0.3 g of anhydrous CDCH is dissolved in 6 ml of water:ethanol (1:1). The solution is heat treated at 70° C. until the solvent has evaporated completely. The crystals which have precipitated out are dried at room temperature in vacuo and then left to stand at room temperature/85% relative humidity overnight.

Example 5 (Needles)

0.1 g of anhydrous CDCH is dissolved in 5 ml of methanol. The solution is left to stand at RT until the solvent has evaporated completely. The crystals are dried in vacuo at room temperature and then left to stand at room temperature/85% relative humidity overnight.

Example 6 (needles)

0.1 g of anhydrous CDCH is dissolved in 5 ml of water. The solution is left to stand at room temperature until the solvent has evaporated completely. The crystals are dried at room temperature in vacuo and then left to stand at room temperature/85% relative humidity overnight.

Example 7

25.1 g of CDCH monohydrate (prisms), 3.3 g of Avicel PH 101 and 1.7 g of maize starch are mixed in a highshear mixer and then granulated with 13 g of water. After rasping (4 mm), the granules are dried in a mini-fluidized bed dryer (intake air temperature 80° C.) and sieved over a 0.8 mm sieve. Subsequent mixing is carried out with 0.19 g of Ac—Di—Sol and 0.01 g of magnesium stearate. The mixture is then pressed on a single punch tabletting machine (tablet format 5.5 r 9, tablet weight 68.5 mg).

Example 8

196.6 g of micronized CDCH monohydrate (needles) are mixed with 88 g of Avicel in a highshear mixer (powder mixture). 3.6 g of PVP 25 are dissolved in 97.2 g of water (granulating liquid). The powder mixture is granulated with the granulation liquid. After rasping (3 mm), the granules are dried in a dryer (intake air temperature 90° C.) and sieved over a 1 mm sieve. Subsequent mixing is carried out with 1.8 g of Ac—Di—Sol and 0.1 g of magnesium stearate. The mixture is then pressed on a rotary press (tablet format 5.5 r 9, tablet weight 83.4 mg).

TABLE 1

| Ir spectroscopy | |
|---|---|
| Anhydrous form [cm$^{-1}$] | Hydrate [cm$^{-1}$] |
| 722 | 722 |
| 804 | 804 |
| 834 | 835 |
| 938 | 875 |
| 957 | 938 |
| 994 | 994 |
| 1048 | 1045 |
| 1186 | 1082 |
| 1319 | 1163 |
| 1354 | 1184 |
| 1372 | 1319 |
| 1453 | 1352 |
| 1513 | 1372 |
| 1622 | 1394 |
| 1709 | 1432 |
| 2427 | 1456 |
| 2524 | 1517 |
| 2700 | 1624 |
| 2929 | 1709 |
| 3469 | 2427 |
| 3527 | 2456 |

TABLE 1-continued

| Ir spectroscopy | |
|---|---|
| Anhydrous form [cm$^{-1}$] | Hydrate [cm$^{-1}$] |
| | 2524 |
| | 2634 |
| | 2925 |
| | 2698 |
| | 2745 |
| | 2893 |
| | 2925 |
| | 3472 |
| | 3530 |

TABLE 2

| X-ray diffractometry | |
|---|---|
| Anhydrous form [2 Theta] | Hydrate [2 Theta] |
| 5,8 | 5,8 |
| 8,6 | 8,5 |
| 10,3 | 10,1 |
| 11,6 | 11,6 |
| 13,6 | 13,4 |
| 14,5 | 14,5 |
| 15,0 | 14,8 |
| 15,8 | 15,6 |
| 17,3 | 17,0 |
| 17,5 | 17,2 |
| 18,3 | 17,4 |
| 18,9 | 17,5 |
| 19,3 | 17,9 |
| 19,6 | 18,6 |
| 20,6 | 19,1 |
| 21,5 | 19,6 |
| 22,5 | 20,4 |
| 22,8 | 21,1 |
| 23,0 | 21,8 |
| 23,8 | 22,7 |
| 24,2 | 23,0 |
| 24,7 | 23,6 |
| 25,0 | 24,1 |
| 26,3 | 24,5 |
| 27,0 | 26,5 |
| 27,4 | 26,7 |
| 27,8 | 27,0 |
| 28,2 | 27,3 |
| 29,4 | 27,5 |
| 29,7 | 27,8 |
| 30,0 | 28,5 |
| 30,3 | 28,9 |
| 31,3 | 29,2 |
| 31,8 | 29,7 |
| 34,5 | 31,4 |
| 35,3 | 31,9 |
| 37,1 | 32,3 |
| | 32,6 |
| | 34,2 |
| | 35,1 |
| | 35,5 |
| | 36,8 |
| | 37,5 |

TABLE 3

$^{13}C$ solid-state NMR spectroscopy

| Anhydrous form [ppm] | Hydrate [ppm] |
|---|---|
| 8,5 | 7,7 |
| 12,3 | 8,3 |
| 14,1 | 9,0 |
| 18,2 | 10,8 |
| 20,0 | 12,1 |
| 22,8 | 18,2 |
| 35,2 | 19,8 |
| 39,7 | 22,9 |
| 46,5 | 34,9 |
| 49,5 | 40,2 |
| 52,3 | 47,0 |
| 55,9 | 49,5 |
| 59,2 | 50,1 |
| 62,6 | 52,6 |
| 65,8 | 55,9 |
| 105,4 | 56,8 |
| 108,1 | 59,4 |
| 116,9 | 64,1 |
| 117,5 | 66,8 |
| 134,7 | 105,0 |
| 136,0 | 107,1 |
| 137,3 | 116,3 |
| 140,1 | 117,4 |
| 142,6 | 135,2 |
| 150,1 | 136,1 |
| 152,6 | 137,4 |
| 165,3 | 140,8 |
| 166,0 | 143,5 |
| 175,5 | 149,3 |
|  | 150,9 |
|  | 168,1 |
|  | 175,5 |

TABLE 4

Raman spectroscopy

| Anhydrous form [cm$^{-1}$] | Hydrate [cm$^{-1}$] |
|---|---|
| 110 | 109 |
| 147 | 148 |
| 243 | 243 |
| 278 | 278 |
| 388 | 309 |
| 425 | 425 |
| 496 | 496 |
| 543 | 543 |
| 723 | 724 |
| 833 | 833 |
| 964 | 962 |
| 1031 | 1031 |
| 1191 | 1191 |
| 1267 | 1305 |
| 1305 | 1321 |
| 1320 | 1352 |
| 1354 | 1376 |
| 1376 | 1433 |
| 1433 | 1490 |
| 1491 | 1554 |
| 2891 | 1619 |
| 2922 | 1711 |
| 2957 | 2835 |
| 2991 | 2888 |
| 3020 | 2923 |
| 3054 | 2942 |
| 3069 | 2958 |
| 3082 | 2977 |
| 3088 | 2990 |
| 3110 | 3019 |
|  | 3056 |

TABLE 4-continued

Raman spectroscopy

| Anhydrous form [cm$^{-1}$] | Hydrate [cm$^{-1}$] |
|---|---|
|  | 3069 |
|  | 3089 |
|  | 3106 |

TABLE 5

FIR spectroscopy

| Anhydrous form [cm$^{-1}$] | Hydrate [cm$^{-1}$] |
|---|---|
| 137 | 95 |
| 165 | 111 |
| 187 | 139 |
| 219 | 145 |
| 230 | 163 |
| 248 | 185 |
| 279 | 220 |
| 289 | 230 |
| 311 | 277 |
| 342 | 313 |
| 370 | 340 |
| 386 | 369 |
| 396 | 388 |
| 412 | 399 |
| 423 | 412 |
| 436 | 423 |
| 456 | 436 |
| 474 | 459 |
| 494 | 476 |
|  | 494 |

We claim:

1. Monohydrate of CDCH, of the formula

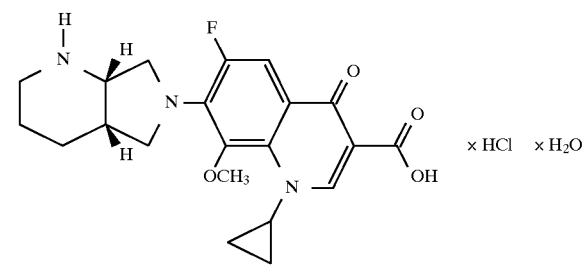

which has a characteristic peak at 168.1 ppm in the $^{13}$C-NMR spectrum and a band at 2Θ=26.7 in the X-ray diffractogram.

2. Compound according to claim 1 in the prismatic crystal form.

3. Process for the preparation of the CDCH monohydrate according to claim 1, characterized in that anhydrous CDCH is treated with an amount of water which is at least sufficient for thorough mixing and hydration until the stoichiometric content of water of crystallization has been absorbed and conversion of the crystals is complete, the crystals of the monohydrate thus obtained are separated off and the adsorbed water present is removed.

4. Process according to claim 3, characterized in that a suspension of the anhydrous CDCH in aqueous media is stirred until hydration and conversion of the crystals is complete.

5. Process according to claim 3, characterized in that, to prepare the monohydrate in the form of prisms, anhydrous CDCH or CDCH monohydrate in the form of needles is dissolved in media having a water content which is stoichiometrically sufficient but limited to 10%, and the solvent is then removed.

6. Process according to claim 3, characterized in that anhydrous CDCH is exposed to humidity until the crystals have been converted quantitatively.

7. An antibacterial composition comprising an antibacterially effective amount of a compound according to claim 1 and a pharmaceutically acceptable carrier.

8. An antibacterial composition comprising an antibacterially effective amount of a compound according to claim 2 and a pharmaceutically acceptable carrier.

9. A method of combating bacteria in a patient comprising administering to said patient an antibacterially effective amount of a compound according to claim 1.

10. A method of combating bacteria in a patient comprising administering to said patient an antibacterially effective amount of a compound according to claim 2.

* * * * *